United States Patent [19]
Crystal

[11] Patent Number: 5,989,521
[45] Date of Patent: *Nov. 23, 1999

[54] METHOD FOR AUGMENTING A DECREASED LEVEL OF REDUCED GLUTATHIONE IN THE LUNG

[75] Inventor: Ronald G. Crystal, Potomac, Md.

[73] Assignee: The United States of America as represented by the Department of Health and Human Services, Washington, D.C.

[*] Notice: This patent is subject to a terminal disclaimer.

[21] Appl. No.: 07/814,885

[22] Filed: Dec. 31, 1991

Related U.S. Application Data

[63] Continuation-in-part of application No. 07/441,521, Nov. 24, 1989, Pat. No. 5,238,683.

[51] Int. Cl.[6] .................................................... A61K 9/12
[52] U.S. Cl. .............................. 424/43; 424/45; 424/46; 424/434; 514/21
[58] Field of Search ................................ 424/43, 45, 46, 424/489, 490; 8/434; 514/2, 8, 18, 21; 530/331

[56] References Cited

U.S. PATENT DOCUMENTS

| | | | |
|---|---|---|---|
| 4,424,216 | 1/1984 | Cerami | 514/351 |
| 4,598,065 | 7/1986 | Lündt | 514/12 |

FOREIGN PATENT DOCUMENTS 0909679  9/1972  Canada.

*Primary Examiner*—Gollamudi S. Kishore
*Attorney, Agent, or Firm*—Leydig, Voit & Mayer, Ltd.

[57] ABSTRACT

The present invention relates, in general, to a method for augmenting reduced glutathione level in the lungs of patients. In particular, the present invention relates to a method for augmenting reduced glutathione level in the lungs of patients with cystic fibrosis (CF), acquired immunodeficiency syndrome (AIDS), or idiopathic pulmonary fibrosis (IPF).

15 Claims, 7 Drawing Sheets

METHOD FOR AUGMENTING A DECREASED LEVEL OF REDUCED GLUTATHIONE IN THE LUNG

BACKGROUND OF THE INVENTION

This application is a continuation-in-part of application Ser. No. 07/441,521 filed Nov. 24, 1989, now U.S. Pat. No. 5,238,683, the contents of which are incorporated herein by reference.

FIELD OF THE INVENTION

The present invention relates, in general, to a method for augmenting reduced glutathione level in the lungs of patients. In particular, the present invention relates to a method for augmenting reduced glutathione level in the lungs of patients with cystic fibrosis (CF), acquired immunodeficiency syndrome (AIDS), or idiopathic pulmonary fibrosis (IPF).

BACKGROUND INFORMATION

In the lung, reduced glutathione (GSH) is present in high concentrations in the epithelial lining fluid (ELF) of the lower respiratory tract, with normal levels in human ELF being more than 40-fold greater than that in plasma. As such, ELF GSH is a major component of the antioxidant screen that protects the pulmonary epithelium from oxidants released by inflammatory cells as well as inhaled oxidants. In addition, ELF GSH helps maintain the normal function of the immune components of the pulmonary epithelial host defense system. However, in certain conditions, such as (1) cystic fibrosis (CF), (2) acquired immunodeficiency syndrome (AIDS), and (3) idiopathic pulmonary fibrosis (IPF), there is found to be a substantial ELF GSH deficiency.

1. CYSTIC FIBROSIS

Cystic fibrosis (CF), the most common lethal hereditary disorder of Caucasians, is caused by mutations of the cystic fibrosis transmembrane conductance regulator (CFTR) gene (Rommens, J. M. et al. (1989) *Science* 245:1059–1065; Riordan, J. R. et al. (1989) *Science* 245:1066–1073; Kerem, B-S. et al. (1989) *Science* 245:1073–1080). The clinical manifestations of CF are characterized by chronic purulent bronchitis, pancreatic insufficiency, and high levels of sodium chloride in sweat (Boat, T. F. et al. (1989) In The Metabolic Basis of Inherited Diseases. C. R. Scriver et al. eds. McGraw-Hill, New York. 2649–2680). Although the disease manifests in several organ systems, the lethal manifestations of CF are usually related to the epithelial surface of the airways. For reasons not completely defined, mutations of the CFTR gene are associated with abnormalities in airway mucus, colonization of the airway epithelium with *Pseudomonas* and other bacteria, and intense local neutrophil-dominated inflammation (Boat, T. F. et al. (1989) In The Metabolic Basis of Inherited Diseases. C. R. Scriver et al. eds. McGraw-Hill, New York. 2649–2680; McElvaney, N. G. et al. (1991) *Lancet.* 337:392–394; Elborn, J. S., and D. J. Shale (1990) *Thorax* 45:970–973; Suter, S. (1989) *In Pseudomonas aeruginosa* Infection, Antibiotic Chemother. N. Hoiby et al. eds. Basel, Karger. 42:158–168). It is the inflammation that is responsible for the progressive derangements to the epithelium, with eventual development of bronchiectasis and loss of functioning alveoli.

In the context that consequent to the neutrophil-dominated inflammation there is a chronic burden of oxidants on the respiratory epithelium, and with the knowledge that oxidants released from inflammatory cells can derange the respiratory epithelial structure and function and interfere with host defense (Elborn, J. S., and D. J. Shale (1990) *Thorax* 45:970–973; Roum, J. H. et al. (1990) *Clin. Res.* 38:440A. (Abstr.); Abramson, S. L. et al. (1991) In The Lung: Scientific Foundations. R. G. Crystal and J. B. West, editors. Raven Press, New York. 553–563; Cantin, A. M. et al. (1987) *J. Clin. Invest.* 79:1665–1673; Warren, J. S. et al. (1991) In The Lung: Scientific Foundations. R. G. Crystal and J. B. West, editors. Raven Press, New York. 1829–1838; El-Haj, A. et al. (1986) *J. Immunol.* 136:3420–3426), the present invention evaluates the status of reduced glutathione (L-$\gamma$-glutamyl-L-cysteinyl-glycine, GSH), in ELF in adults with CF. In normal individuals, respiratory ELF has high levels of GSH, typically 50-fold greater than plasma (Cantin, A. M. et al. (1987) *J. Appl. Physiol.* 63:152–157). GSH can scavenge all major oxidants produced by inflammatory cells (Meister, A. (1988) *J. Biol. Chem.* 263:17205–17208; Buhl, R. et al. (1990) *Proc. Natl. Acad. Sci. USA.* 87:4063–4067; Heffner, J. E., and J. E. Repine (1989) *Am. Rev. Respir. Dis.* 140:531–554), and its function as an antioxidant on the respiratory epithelial surface is enhanced by the presence of glutathione peroxidase and glutathione reductase in respiratory ELF (Meister, A. (1988) *J. Biol. Chem.* 263:17205–17208; Cantin, A. M. et al. (1990) *J. Clin. Invest.* 86:962–971; Davis, W. B., and E. R. Pacht (1991) In The Lung: Scientific Foundations. R. G. Crystal and J. B. West, editors. Raven Press, New York. 1821–1828).

2. AIDS

One major manifestation of AIDS is the development of opportunistic infections in the lung (Levy, J. A., ed. (1990) AIDS: Pathogenesis and Treatment, New York, New York, Marcel Dekker; Murray, J. F., and J. Mills (1990) Am Rev Resp Dis 141:1356–1372). Progression from human immunodeficiency virus (HIV)-seropositivity to AIDS is manifested initially by lung infection in greater than 60% of affected individuals, and more than 80% of all opportunistic infections associated with AIDS occur in the lung (Levy, J. A., ed. (1990) AIDS: Pathogenesis and Treatment, New York, New York, Marcel Dekker; Murray, J. F., and J. Mills (1990) Am Rev Resp Dis 141:1356–1372). While depletion of CD4+ T-cells plays an important role in the pathogenesis of AIDS, the extent of immune abnormalities in healthy HIV-seropositive individuals with normal numbers of CD4+ T-cells suggests there must be additional mechanisms contributing to the development of the immune dysfunction associated with HIV infection (Fauci, A. S. (1988) Science 239:617–622; Levy, J. A. (1988) Nature 333:519–522; Edelman, A. S., and S. Zolla-Panzer (1989) FASEB J 3:22–30).

One such mechanism may be the observed deficiency of the antioxidant and immune enhancing tripeptide glutathione (L-$\gamma$-glutamyl-L-cysteinyl-glycine) (Meister, A., and M. E. Anderson (1983) Ann Rev Biochem 52:711–760; Meister, A. (1988) J Biol Chem 263:17205–17226). In symptom-free HIV-seropositive individuals, plasma glutathione levels are about 30%, ELF glutathione levels are about 60%, of the levels in normal individuals (Buhl, R. et al (1989) Lancet 2:1294–1298). This deficiency of glutathione may be relevant to the pathogenesis of the immunodeficiency associated with HIV infection in several ways. First, as an antioxidant which efficiently scavenges intracellular and extracellular toxic oxygen radicals, a deficiency of GSH allows these unchecked oxygen products to damage immune cell function (Carson, D. A. et al. (1986) J. Exp Med 163:746–751; El-Hag, A. et al. (1986) J Immunol 136:3420–3426; Stagnaro, R. et al. (1987) Bull Eur Physiopathol Respir 23:303–307). Second, as a metabolite or cofactor in a variety of normal immune cell processes, a deficiency of glutathione inhibits lymphocyte activation and effector functions, as well as causing dysfunction of natural killer cells and lymphocyte-mediated cytotoxicity (Suthanthiran, M. et al. (1990) Proc Natl Acad Sci USA 87:3343–3347; Messina, J. P., and D. A. Lawrence (1989) J Immunol 143:1974–1981; Liang, C-M. et al. (1989) J Biol Chem 264:13519–13523; Liang, C-M. et al (1990) Sixth International Conference on AIDS 336. (Abstr.), see also Buhl, R. et al (1989) Lancet 2:1294–1298 for review). Finally, recent observations suggest intracellular glutathione deficiency may permit more rapid growth of the HIV virus (Roederer, M. et al (1990) Proc Natl Acad Sci USA 87:4884–4888; Kalebic, T. et al. (1991) Proc Natl Acad Sci USA 88:1906–1910). The glutathione deficiency observed in HIV-seropositive individuals may be particularly consequential for host defense in the lung, as glutathione concentrations in normal lung ELF are more than 40-fold greater than that in plasma, suggesting a relatively important contribution of glutathione to the respiratory epithelium both as an antioxidant and to maintain the normal function of the immune cells of the pulmonary host defense system (Cantin, A. M. et al. (1987) J Appl Physiol 63:152–157; Heffner, J. E., and J. E. Repine (1989) Am Rev Resp Dis 140:531–554).

3. IDIOPATHIC PULMONARY FIBROSIS

Idiopathic pulmonary fibrosis (IPF; also referred to "cryptogenic fibrosing alveolitis"), a progressive fatal interstitial lung disorder, is characterized by the accumulation of inflammatory cells in the lower respiratory tract, including activated alveolar macrophages and neutrophils, alveolar epithelial injury and progressive interstitial fibrosis (Crystal, R. G. et al. (1984) N. Engl. J. Med. 310: 154–166, and 310: 235–244; Turner-Warwick, M. et al. (1980) Thorax. 35: 171–180). The exaggerated release of oxygen radicals (oxidants) by the inflammatory cells plays a central role in the alveolar epithelial injury that typifies IPF (Cantin, A. M. et al. (1987) J. Clin. Invest. 79: 1665–1673). The oxidant-antioxidant imbalance on the respiratory epithelial surface is further compounded in IPF by a deficiency in ELF levels of GSH (Cantin, A. M. et al. (1989) Am. Rev. Resp. Dis. 139: 370–372).

With this background, it is reasonable to consider administering glutathione to augment GSH levels in individuals with a condition such as CF, AIDS, or IPF. However, while the concept of augmenting GSH levels is rational, in practice it is difficult to achieve. The problem is not how to obtain the GSH—it is readily synthesized by chemical methods—but how to deliver it systemically. Oral administration of glutathione would lead to gastric degradation by peptidases. Intravenous administration is possible, but impractical, as the serum half-life of glutathione is <2 min (Wendel, A., and P. Cikryt (1980) FEBS Letters 120:209–211). As a potential solution to these problems, the present invention provides a method of targeting glutathione to the lung by aerosol delivery.

SUMMARY OF TEE INVENTION

It is a general object of this invention to provide a method for augmenting reduced glutathione level in the lungs of patients.

It is a specific object of this invention to provide a method for augmenting reduced glutathione level in the lungs of patients with cystic fibrosis, acquired immunodeficiency syndrome, or idiopathic pulmonary fibrosis.

Further objects and advantages of the present invention will be clear from the description that follows.

DETAILED DESCRIPTION OF THE INVENTION

Figure 1:
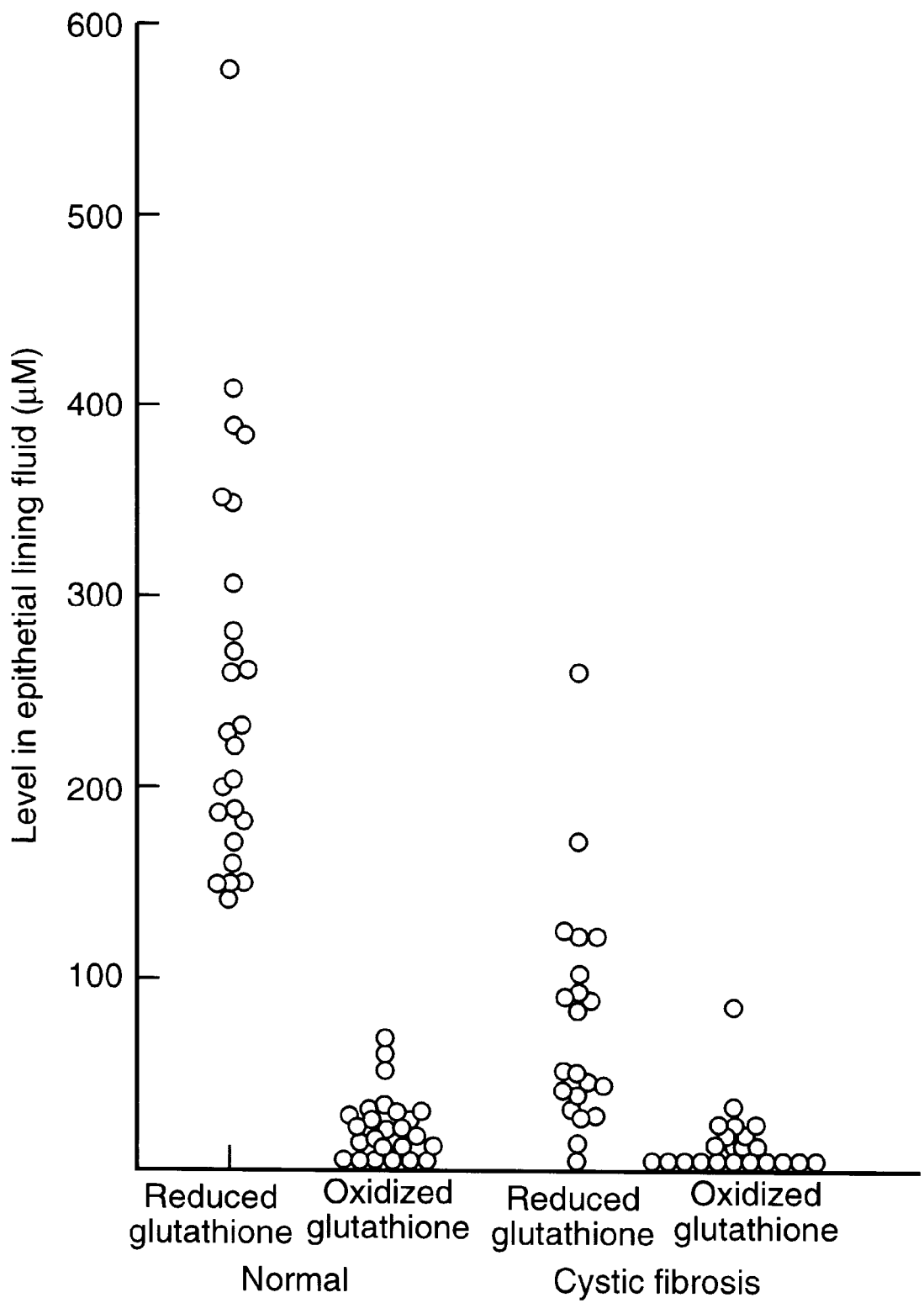
FIG. 1. Glutathione levels in respiratory ELF. Shown is the level of reduced and oxidized glutathione in ELF for normals and individuals with cystic fibrosis. Each data point represents the average value of duplicate determinations for a single individual.
Figure 2:
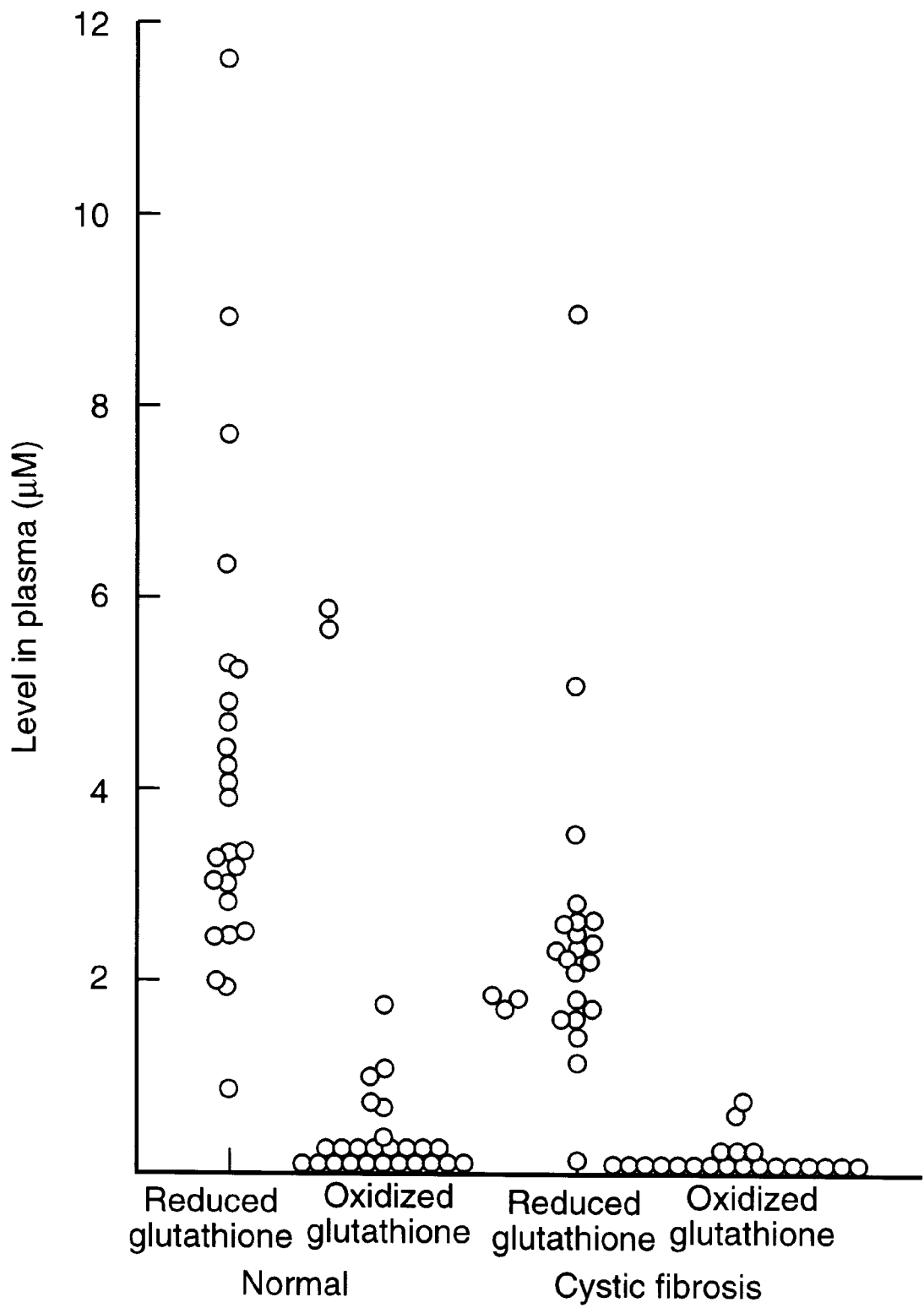
FIG. 2. Glutathione levels in plasma. Shown is the level of reduced and oxidized glutathione in plasma for normals and individuals with cystic fibrosis. Each data point represents the average value of duplicate determinants for a single individual.

The present invention relates to a method for augmenting reduced glutathione level in the lungs.

In one embodiment, the present invention relates to a method for augmenting reduced glutathione level in the lungs of patients with CF, AIDS, or IPF. The method comprises administering through inhalation to the lungs of the patient an aerosol of GSH. The aerosol comprises an effective amount of reduced glutathione in a pharmaceutically acceptable carrier.

In one preferred embodiment, the aerosol comprises about 10 mg to about 2,500 mg of GSH in about 0.9% in terms of weight by volume sterile, sodium chloride solution. In another preferred embodiment, the aerosol comprises about 10 mg to about 25 mg of GSH in 1 to 5 ml of a suitable carrier. Suitable carriers include powder inhalents and water soluble carriers. The aerosol is preferrably contained in a sterile pneumatic aerosol generator reservoir, so that an aerosol of said GSH is produced at the rate of about 8–12 liters per minute at about 30–50 psi of compressed air. In a more preferred embodiment, the aerosol is produced at about 10 liters per minute at about 40 psi of the compressed air.

The frequency of administration can be readily determined by one skilled in the art. In one preferred embodiment, the aerosol is delivered 1 to 4 times daily. Appropriate dosing can be determined by sampling epithelial lining fluid of the lung by bronchoalveolar lavage and quantifying the amount of glutathione present.

Additional disease states that can be treated with the aerosol include any infectious or inflammatory lung disorder including but not limited to bronchitis, pneumonia, emphysema, adult respiratory distress syndrome, respiratory distress syndrome of newborn, and the interstitial lung diseases.

The present invention is described in further detail in the following non-limiting Examples.

EXAMPLE 1

CF PATIENT ANALYSIS

I. Protocols and Experimental Details for CF Patients

Study Population. The study population consisted of 21 individuals with cystic fibrosis (12 male, 9 female, mean age 27±2 yr) (all data are presented as mean ± standard error of the mean; all statistical comparisons were made using the two-tailed Student's t-test.), defined by typical clinical presentation and abnormal sweat chloride tests (Boat, T. F. et al. (1989) In The Metabolic Basis of Inherited Diseases. C. R. Scriver et al. eds. McGraw-Hill, New York. 2649–2680). All had *Pseudomonas* in the sputum. Lung function tests (Fulmer, J. D. et al. (1977) *J. Clin. Invest.* 60:595–610) were typical for young adults with moderate disease (Table I). For comparison, 25 non-smoking normal individuals were evaluated (17 male, 8 female, mean age 34±2). Serum aspartate transferase (AST), alanine transferase (ALT) and γ-glutamyltransferase levels were measured in all individuals; 1/21 CF individuals had a mild elevation in AST, 1/21 had a mild elevation in ALT; and 3/21 had mild elevations in γ-glutamyltransferase.

Bronchoalveolar Lavage and Plasma Samples. Bronchoalveolar lavage was carried out as previously described (Saltini, C. et al. (1984) *Am. Rev. Resp. Dis.* 130:650–658). The cells were separated from the lavage fluid by centrifugation and total cell number and cell differential determined. Aliquots of the lavage fluid were taken for glutathione and urea measurements. Venous blood samples for plasma glutathione and urea were obtained in the fasting state.

Glutathione Measurement. Total and oxidized glutathione levels in ELF and venous plasma were quantified in duplicate as previously described (Buhl, R. et al. (1989) *Lancet* 2:1294–1298; Borok, Z. et al. (1991) *Lancet* 338:215–216). For total glutathione, 10 mM 5,5'-dithio-bis-(2-nitrobenzoic acid) (DTNB, Sigma, St. Louis, Mo.) was added to an equal volume of sample. The rate of reduction of DTNB was measured spectrophotometrically (412 nm, Beckman DU-70, Beckman Instruments, Fullerton, Calif.) in the presence of 0.5 U/ml glutathione reductase (Sigma) and of 220 nM β-nicotinamide adenine dinucleotide phosphate (NADPH, Sigma). Determination of the total glutathione concentration was based on standard curves generated with known concentrations of oxidized glutathione (0.125 to 4 μM).

To quantify levels of oxidized glutathione (GSSG), 10 mM N-ethylmaleimide (Sigma) was added to an equal volume of sample, which was then passed through a SEP-PAK C18 cartridge (Waters, Milford, Mass.). DTNB, glutathione reductase, and NADPH were then added to the same final concentrations as described above, and the rate of reduction of DTNB was measured spectrophotometrically at 412 nm using similar standard curves.

The amount of GSH in each sample was determined by subtracting the amount of oxidized glutathione from the total glutathione. All values were referenced to volume of ELF as assessed by the urea method (Rennard, S. I. et al. (1986) *J. Appl. Physiol.* 60:532–538).

II. Results

Cellular Composition of Epithelial Lining Fluid. The relative amount of lavage fluid recovered from individuals with CF was similar to that from normals (p>0.9, Table I). The total number of inflammatory cells in cystic fibrosis ELF was markedly elevated in comparison to normals (p<0.001). Furthermore, the inflammatory cell profile was very different in cystic fibrosis compared to normals, with a vast increase in the proportion of neutrophils (p<0.001) and a decrease in the proportion of macrophages (p<0.001) and lymphocytes (p<0.001). When evaluated in terms of "cell density" in ELF (the total number of each cell type/μl ELF), it was evident that CF ELF was characterized by 9-fold greater density of total inflammatory cells (p<0.001), a 380-fold increase in neutrophils (p<0.001) and a 3-fold increase in macrophages (p<0.001).

Levels of Reduced and Oxidized Glutathione in ELF. The amount of total glutathione was decreased in CF ELF compared to normal individuals (CF 92±14 μM; normal 278±21 μM; p<0.001). This was due to a reduction in reduced glutathione. The amount of GSH in CF was markedly deficient in CF ELF compared to normal individuals (CF 78±13 μM; normal 257±21 μM; p<0.001, FIG. 1). In contrast, the amount of GSSG was the same in CF ELF and normal individuals (CF 14±4 μM; normals 21±4 μM, p>0.2).

Levels of Reduced and Oxidized Glutathione in Plasma. As in ELF, the amount of total glutathione was decreased in CF plasma compared to normal individuals (CF 2.7±0.4 μM; normal 4.5±0.5 μM; p<0.005). Similar to that observed in ELF, this was due to a reduction in reduced glutathione. The amount of GSH was deficient in CF plasma compared to normal individuals (CF 4.3±0.5 μM; normal 2.6±0.4 μM; p<0.02), but the amount of GSSG was the same in CF plasma and normal individuals (0.1±0.1 and 0.3±0.1 μM respectively, p>0.08; FIG. 2).

TABLE I

Lung Function and Bronchoalveolar Lavage Parameters in Cystic Fibrosis and Normals

|  | Normal | Cystic fibrosis[3] |
|---|---|---|
| Lung function (% predicted)[2] | | |
| VC | 95 ± 2[1] | 62 ± 3 |
| TLC | 94 ± 2 | 73 ± 3 |
| FEV1 | 100 ± 2 | 46 ± 3 |
| FEV1/FVC | 110 ± 2 | 77 ± 4 |
| DLCO | 96 ± 3 | 77 ± 4 |
| Bronchoalveolar lavage | | |
| % Lavage fluid recovered | 55 ± 2 | 55 ± 3 |
| Total cells recovered ($\times 10^4$/ml lavage fluid recovered) | 12.2 ± 0.9 | 223 ± 35 |
| ELF volume recovered (ml/100 ml lavage fluid recovered) | 1.1 ± 0.1 | 2.1 ± 0.2 |
| Cell differential (%) | | |
| Alveolar macrophages | 88.8 ± 1.3 | 30.6 ± 3.5 |
| Lymphocytes | 8.7 ± 1.1 | 2.5 ± 0.9 |
| Neutrophils | 2.1 ± 0.7 | 66.9 ± 3.9 |
| Eosinophils | 0.4 ± 0.1 | 0.2 ± 0.2 |
| Cells/µl ELF ($\times 10^3$) | 12.3 ± 1.2 | 109.0 ± 14.1 |
| Alveolar macrophages | 11.0 ± 1.0 | 31.3 ± 4.8 |
| Lymphocytes | 1.1 ± 0.2 | 1.2 ± 0.3 |
| Neutrophils | 0.2 ± 0.1 | 76.3 ± 10.8 |
| Eosinophils | 0.1 ± 0.1 | 0.1 ± 0.1 |

[1]All values are expressed as mean ± standard error of the mean.
[2]VC = vital capacity; TLC = total lung capacity by He dilution; FEV1 = forced expiratory volume in 1 sec; FVC = forced vital capacity; DLCO = diffusion capacity of the lung for carbon monoxide, corrected for hemoglobin; see (Fulmer, J. D. et al. (1977) J. Clin. Invest. 60:595–610) for lung function methods and predicted values.
[3]All cystic fibrosis values are different than normal ($p < 0.05$) except for % fluid recovered ($p > 0.9$) and % eosinophils, lymphocytes/ELF, and eosinophils/ELF (all $p > 0.1$).

TABLE II

Summary of Lung Epithelial Lining Fluid and Plasma Glutathione Levels in Various Inflammatory Lung Disorders[1]

| Condition | ELF | Plasma | Reference |
|---|---|---|---|
| Cigarette smoking[2] | ↑ | normal | (4) |
| IPF | ↓ | normal | (5) |
| HIV[3] | ↓ | ↓ | (6) |
| ARDS | ↓ | ↓ | (7) |
| CF | ↓ | ↓ | present study |

[1]ELF = epithelial lining fluid; IPF = idiopathic pulmonary fibrosis; HIV = human immunodeficiency virus infection; ARDS = the adult respiratory distress syndrome; CF = cystic fibrosis; ↑ = increased compared to normal, ↓ = decreased compared to normal.
[2]Individuals that smoke cigarettes but with no clinical evidence of lung disease.
[3]Individuals that are HIV + but asymptomatic, as well as individuals with the acquired immunodeficiency syndrome.
[4]Cantin, A. M. et al. (1987) J. Appl. Physiol. 63:152–157
[5]Borok, Z. et al. (1991) Lancet 338:215–216; Cantin, A. M. et al. (1989) Am. Rev. Respir. Disease. 139:370–372
[6]Buhl, R. et al. (1989) Lancet 2:1294–1298; Buhl, R. et al. (1991) Am. Rev. Respir. Dis. 143:A744. (Abstr.)
[7]Bunnell, E. A. et al. (1991) Am. Rev. Respir. Dis. 143:A714. (Abstr.); Bernard, G. R. et al. (1989) Am. Rev. Respir. Dis. 139:A221. (Abstr.)

EXAMPLE 2

AIDS PATIENT ANALYSIS

I. Protocols and Experimental Details for AIDS Patients

Study Population. The study population included 13 male and 1 female HIV-seropositive individuals (average age 32±2 yr)(all data are presented as mean ± standard error of the mean; all statistical comparisons were made using the two-tailed Student's t-test). The diagnosis of HIV infection was confirmed by ELISA and Western blot analysis. All belonged to defined risk groups (13 homosexuals, 1 with heterosexual contact with an infected partner). None were smokers, 9 were untreated, and 5 were receiving azidothymidine, and two were receiving once monthly pentamidine by aerosol. The average number of blood lymphocytes was 1,430±170 cells/µl, including 279±53 CD4+ lymphocytes/µl. p24 antigen was detected in the sera of 2 individuals. All had normal chest roentgenograms. On the average, lung function tests were normal.

To evaluate possible toxicity of the glutathione aerosol, symptoms, physical examination, routine blood studies, chest x-ray, electrocardiogram, renal function, arterial blood gases, and tests of pulmonary function (forced vital capacity, forced expiratory volume in one second, total lung capacity, diffusing capacity) were followed carefully throughout the study. In addition, visual examination of the respiratory mucosa and analysis of differential cell count in bronchoalveolar lavage fluid were performed before the first aerosol and after administration of the last aerosol.

Biologic Samples. Venous plasma and bronchoalveolar lavage fluid were obtained by standard technique (Saltini, C. et al. (1984) Am Rev Resp Dis 130:650–658). Portions of the lavage fluid were taken for glutathione assays (see below), cell counts (total cell and CD4+ and CD8+ subtypes), and for cytocentrifuge preparations for differential counts. The cells were pelleted and the supernatant was used to quantify the amount of ELF recovered using the urea method (Rennard, S.I. et al. (1986) J Appl Physiol 60:532–538).

Glutathione Preparation. The reduced form of glutathione was obtained as a free acid (tissue culture grade; Sigma) and stored at 4°. All preparations were sterile and pyrogen free as determined by the NIH Pharmaceutical Development Service. The glutathione preparation was >98% pure with the percentage of reduced glutathione (determined prior to each experiment, see below) constantly >96%.

Study Design. Venous plasma and bronchoalveolar lavage fluid were obtained before GSH administration. An aerosol of 600 mg GSH in 4 ml of saline was then administered over a 25 min period twice a day for three days. Following the last aerosol, venous plasma and bronchoalveolar lavage fluid were again obtained at intervals up to 3 hr after the last aerosol. All measurements were carried out in duplicate.

Aerosol Generating System. Reduced glutathione was put into a form capable of reaching the lower respiratory tract with a nebulizer (Ultravent, Mallinckrodt) that generates aerosol droplets of a size appropriate for deposition in the alveolar regions (Buhl, R. et al. (1990) Proc Natl Acad Sci USA 87:4063–4067). To generate the aerosol containing the reduced glutathione, 4 ml of a solution of GSH at a concentration of 150 mg/ml in 0.9% NaCl was placed in the reservoir of the nebulizer, and the nebulizer was driven at 40 psi with compressed air. The size distribution of aerosol droplets determined by laser particle-size analysis demonstrated a mass median aerodynamic diameter of the droplets of 2.8 µm with a geometric standard deviation of 1.3 µm. The relative proportion of the GSH preparation that remained in the reduced form was unchanged (Buhl, R. et al. (1990) Proc Natl Acad Sci USA 87:4063–4067). In this regard, the total glutathione in the pre-aerosol preparations contained 98.2±0.1% glutathione in the reduced form, while the glutathione in the aerosolized droplets was 97.0±0.6% in the reduced form. Together, these observations demonstrate that the aerosol was composed of fully functional reduced glutathione within droplets of an optimal size for reaching the alveolar regions of the lung.

Glutathione Levels and Form. Glutathione levels in venous plasma, and bronchoalveolar lavage fluid were quantified with minor modifications of standard methods, as previously described (Buhl, R. et al (1989) Lancet 2:1294–1298).

T-lymphocyte Proliferation Assays. Cell proliferation in the presence of pre-aerosol compared to post-aerosol concentrations of reduced glutathione was tested on the cytotoxic T-lymphocyte cell lines CT-4R and CTLL-2 (Liang, C-M. et al. (1989) J Biol Chem 264:13519–13523). In 96-well flat bottom plates were placed 50,000 cells of the respective cell lines, suspended in 200 $\mu$l Dulbecco's Modified Eagle Medium with 10% fetal calf serum, with either 150 $\mu$M or 280 $\mu$M reduced glutathione added. The IL-2 dependent cell line CTLL-2 had 0.3 units/ml IL-2 (Genzyme) added in each well. After 18 hr culture in a 10% $CO_2$ incubator at 37° C., 0.5 $\mu$Ci of $^3$H-thymidine was added for 4 hr, followed by harvesting of cells onto glass fiber filters and scintillation counting for 1 minute. All proliferation assays were done in triplicate.

II. Results

Safety Evaluation. No symptoms were noted referable to the aerosol administration of glutathione. Physical examination and all clinical studies remained stable following glutathione therapy. Importantly, pulmonary function tests and arterial blood gases were also unchanged (all parameters p>0.3 compared to baseline). Aerosolization of GSH did not result in inflammation of the lower respiratory tract, as judged by visual inspection of the mucus membranes of the respiratory tract, measurements of ELF volumes of pre- and post-aerosol bronchial lavage fluids or lavage cell differentials (p>0.1, all comparisons to baseline values).

Figure 3:
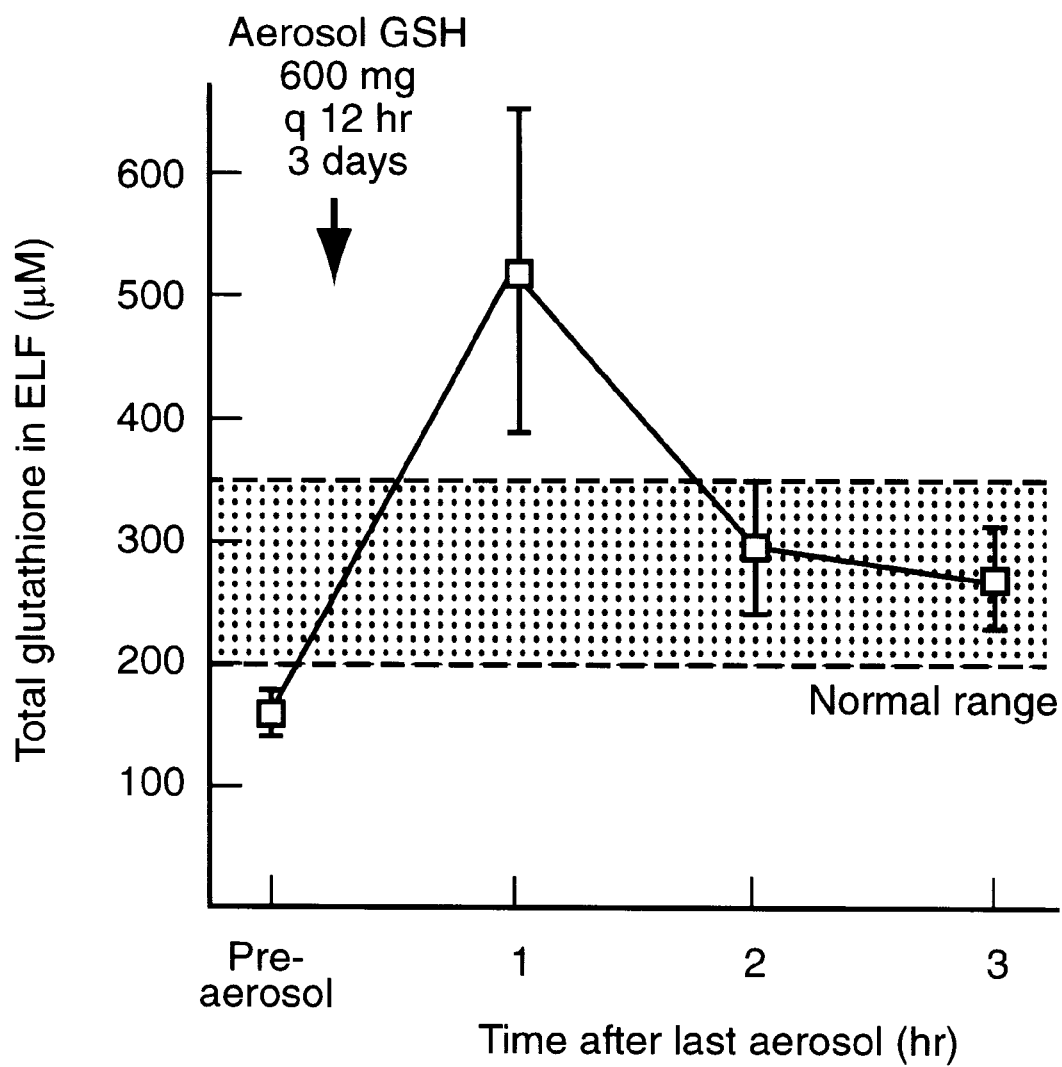
FIG. 3. Total glutathione in lung ELF before and after glutathione aerosol therapy. The concentration of total glutathione in $\mu M$ units is shown pre-aerosol and at 1, 2, and 3 hr after the final aerosol of 600 mg of GSH administered once every 12 hr for 3 days. The shaded region represents the normal range of total glutathione in ELF.

Glutathione Levels Before and After Aerosolization. Pre-therapy, ELF total glutathione levels in the HIV-seropositive group (160±16 $\mu$M) were significantly less than normal (271±14 $\mu$M; p<0.001, FIG. 3). However, following therapy of a total of 6 doses of 600 mg GSH given every 12 hr for three days, ELF total glutathione values rose in each of the 14 individuals evaluated, with the mean ELF total glutathione levels increasing to 520±132 $\mu$M 1 hr after therapy, to 294±56 $\mu$M at 2 hr, and 269±41 $\mu$M at 3 hr. levels above or within the normal range, and all above the pre-therapy value (p<0.005, all values post-therapy compared to pre-therapy).

Figure 4A:
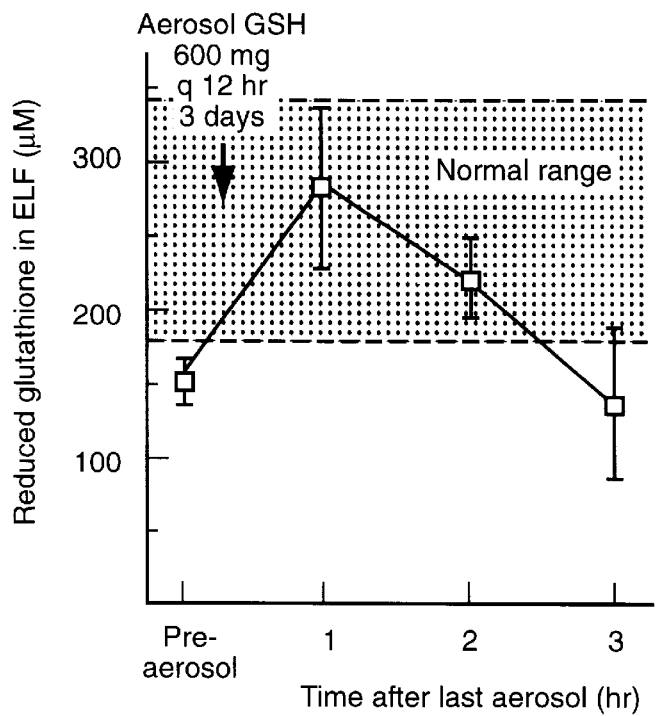
FIGS. 4A and B. Form of glutathione in lung ELF before and after glutathione aerosol therapy. A. Levels of reduced glutathione. The concentration of reduced glutathione in $\mu M$ units is shown pre-aerosol and at 1, 2, and 3 hr after the final aerosol of 600 mg of GSH, administered once every 12 hr for 3 days. The shaded region represents the normal range of reduced glutathione in ELF. B. Oxidized glutathione. The percentage of total glutathione in the form of oxidized glutathione is shown pre-aerosol and at 3 hr after the last aerosol of reduced glutathione.
Figure 4B:
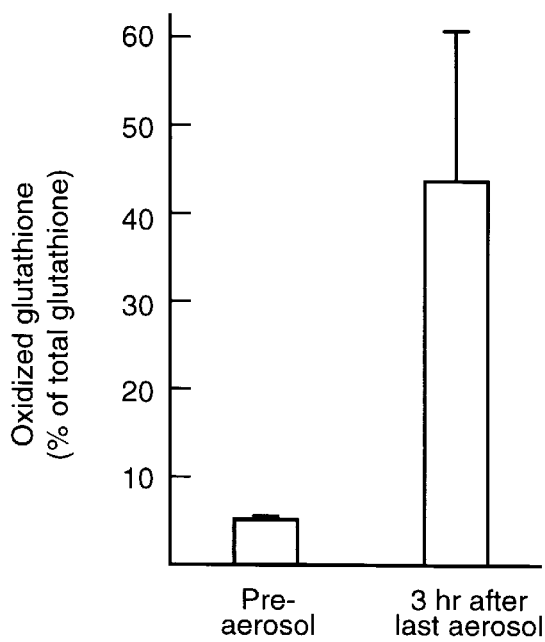

As with total glutathione, the average ELF levels of reduced glutathione in the HIV-seropositive group (153±15 $\mu$M) were significantly less than normal (245±12 $\mu$M; p<0.001). ELF reduced glutathione levels following 3 days of aerosol therapy increased to levels within the normal range at 1 hr (282±56 $\mu$M; p<0.005 compared to pre-therapy levels) and at 2 hr (223±27 $\mu$M; p<0.05), returning to baseline levels of 138±53 $\mu$M at 3 hr (p>0.9) (FIG. 4, panel A). Thus, as expected, before therapy, 95±2% of the total glutathione recovered from ELF was in the reduced form. After therapy, reduced glutathione levels in ELF at each time point were significantly lower than levels of total glutathione (compare FIG. 4A to FIG. 3; p<0.03 comparisons at all time points after therapy). This difference is explained by a dramatic increase in both the absolute amounts and percentage of oxidized glutathione in ELF following therapy. Before therapy, the average level of oxidized glutathione in ELF was 7±1 $\mu$M, rising to 239±83 uM 1 hr after therapy, and remaining elevated during the study period (2 hr: 72±43 uM; 3 hr: 131±69 uM; p<0.005 all values compared to pre-therapy). Expressed as a percentage of total glutathione in ELF, for example at 3 hr, when reduced glutathione had returned to pre-therapy levels, oxidized glutathione represented 44±18% of the total glutathione in ELF (FIG. 4B).

T-lymphocyte Proliferation Assays. The cytotoxic lymphocyte cell line CT-4R increased proliferation from 7478±550 cpm after incubation with the pre-therapy concentration of 150 $\mu$M reduced glutathione to 10,752±376 cpm after incubation with the post-therapy concentration of 280 $\mu$M reduced glutathione (p<0.01). Similarly, the cytotoxic lymphocyte cell line CTLL-2 increased proliferation from 5077±69 cpm in 150 $\mu$M reduced glutathione to 5792±219 cpm in 280 $\mu$M reduced glutathione (p<0.05).

EXAMPLE 3

IPF PATIENT ANALYSIS

I. Protocols and Experimental Details for IPF Patients

Ten individuals with IPF (6 male, 4 female, 46±3 yr) defined by standard clinical criteria (Crystal, R. G. et al. (1984) N. Engl. J. Med. 310: 154–166, and 310: 235–244; Turner-Warwick, M. et al. (1980) Thorax. 35: 171–180) received aerosolized GSH; 19 normal nonsmokers (14 male, 5 female, 36±3 yr) (Buhl, R. et al. (1989) Lancet. 2: 1294–1298) served as controls for GSH levels. Bronchoalveolar lavage (Buhl, R. et al. (1990) Proc. Natl. Acad. Sci. USA. 87:4063–4067; Buhl, R. et al. (1989) Lancet. 2: 1294–1298) showed typical features of macrophage-neutrophil dominated alveolitis in IPF. The glutathione preparation (97±3% reduced form) was reconstituted in 0.9% saline; aerosolization did not alter the form of the GSH (Buhl, R. et al. (1990) Proc. Natl. Acad. Sci. USA. 87:4063–4067). An aerosol of 600 mg GSH was administered every 12 hr for 3 days. Respiratory ELF, obtained by lavage, was evaluated before therapy, and 1 hr after the first or last (sixth) aerosol, and plasma before and 1 hr after the last aerosol. Total glutathione, oxidized glutathione (GSSG) and reduced glutathione (GSH) levels in ELF and plasma were quantified as previously described (Buhl, R. et al. (1990) Proc. Natl. Acad. Sci. USA. 87:4063–4067; Buhl, R. et al. (1989) Lancet. 2: 1294–1298). Spontaneous $O_2^-$ release from adherent alveolar macrophages was measured by the reduction of ferricytochrome C (Buhl, R. et al. (1990) Proc. Natl. Acad. Sci. USA. 87:4063–4067). All data are presented as mean ± standard error of the mean. The two-tailed Student's t-test was used to compare ELF glutathione levels in normal and IPF individuals and the results presented as exact p values and degrees of freedom (df). The Wilcoxon paired nonparametric test was used to compare pre- and post-aerosol therapy ELF GSH levels and spontaneous $O_2^-$ release by alveolar macrophages, and the results presented as exact p values.

II. Results

Figure 5:
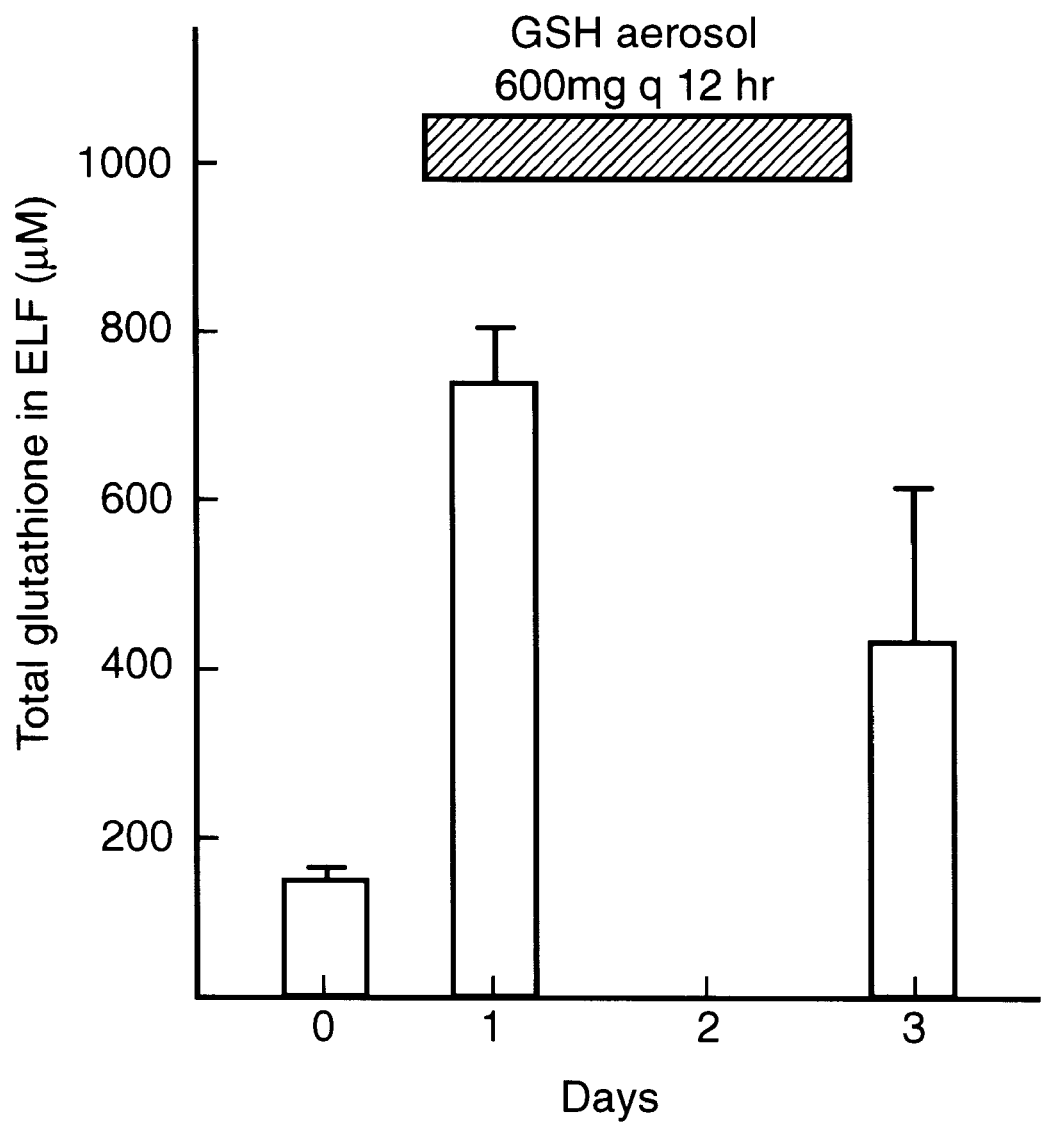
FIG. 5. Effect of aerosolized reduced GSH on ELF total glutathione levels in IPF. GSH (600 mg) was administered by aerosol twice daily for 3 days, and ELF recovered by lavage pretherapy and 1 hr after the first and last aerosol. Concentrations of total glutathione are expressed relative to the volume of ELF recovered.
Figure 6:
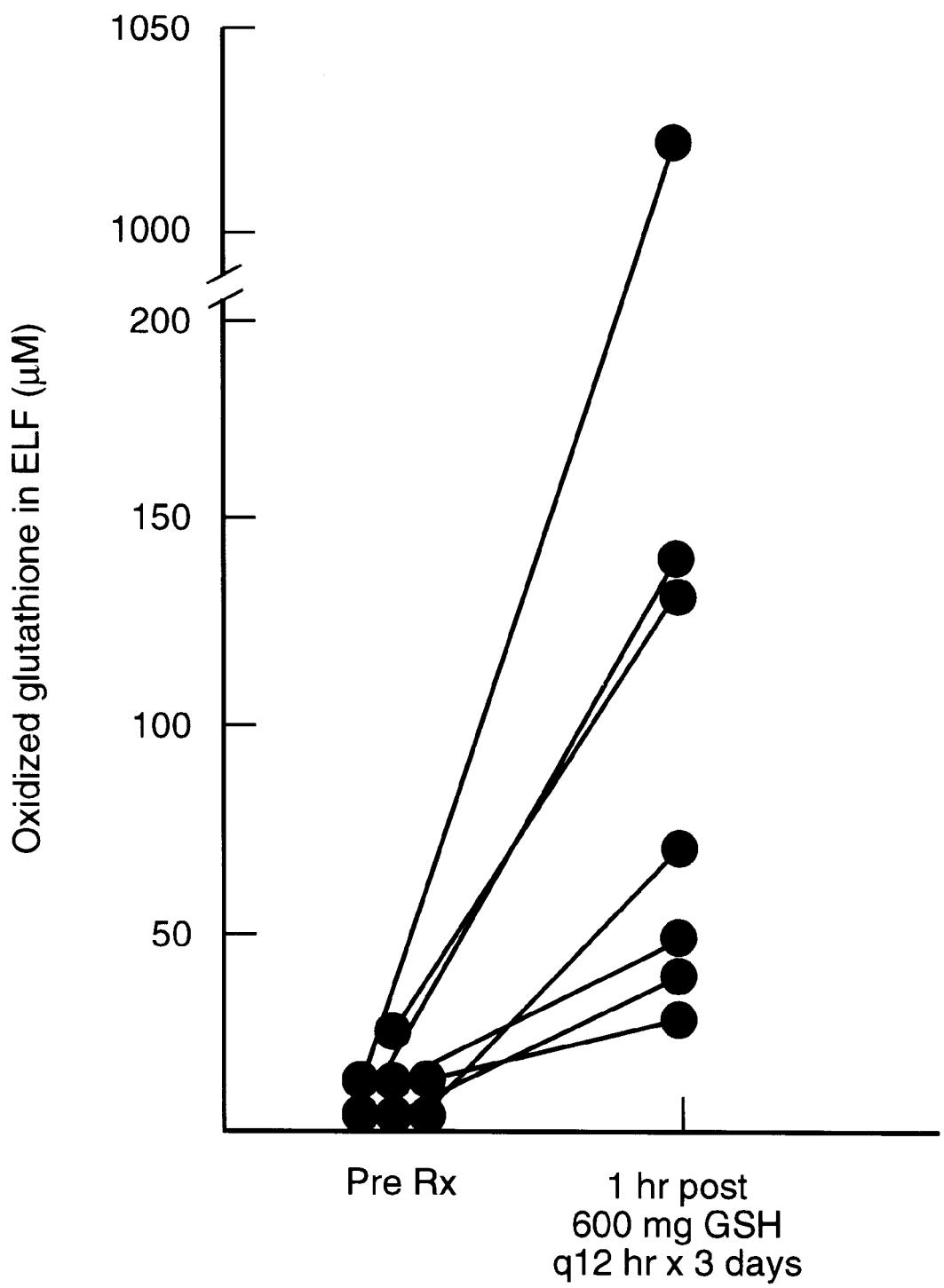
FIG. 6. Oxidized glutathione levels in respiratory ELF in IPF following aerosol administration of reduced GSH (600 mg) administered twice daily for 3 days. ELF was recovered pretherapy and 1 hr after the last dose. Each data point represents the mean of duplicate determinations for one individual. Concentrations of oxidized glutathione are expressed relative to the volume of ELF recovered.
Figure 7:
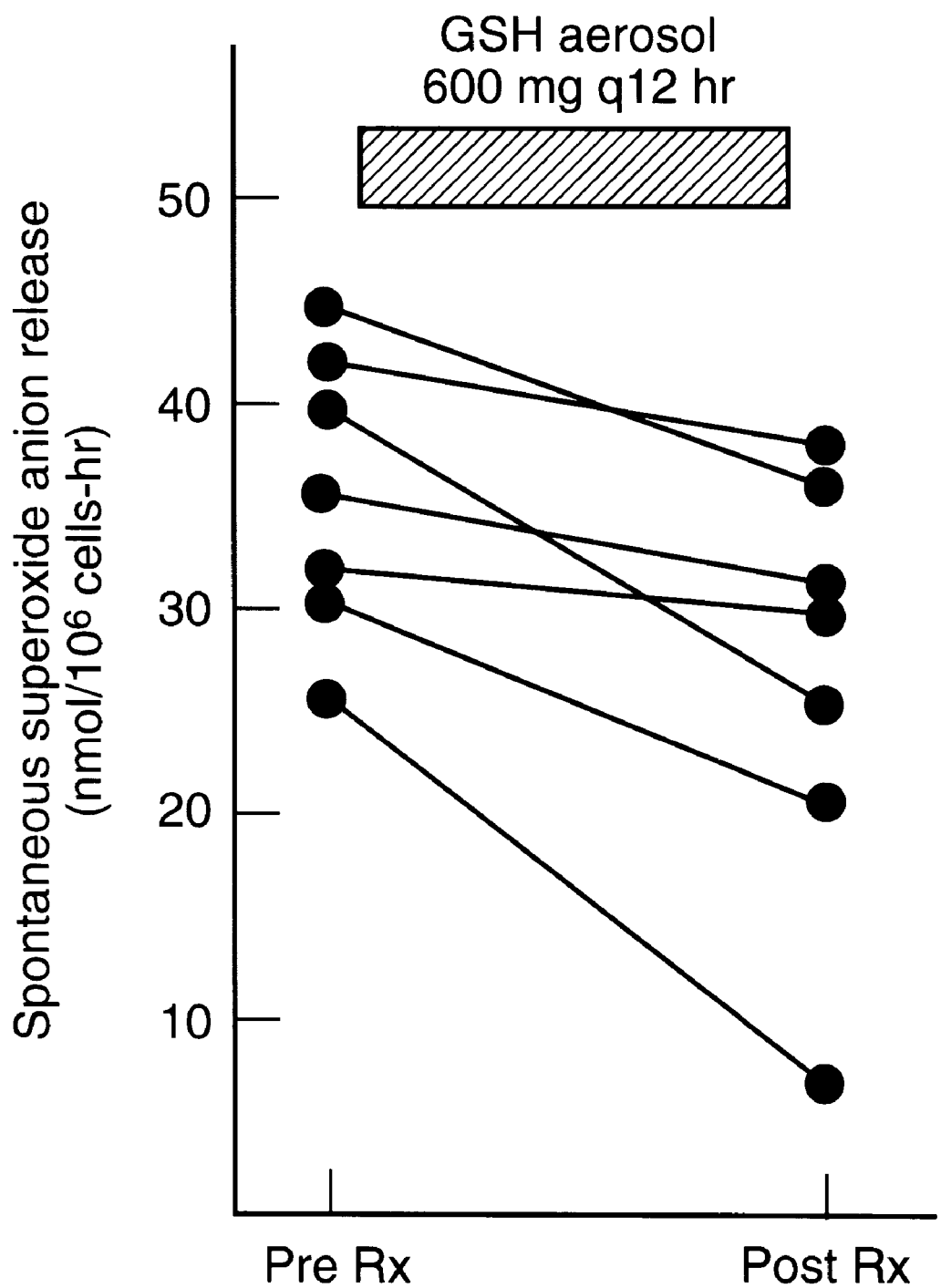
FIG. 7. Spontaneous release of superoxide anion ($O_2^-$) by alveolar macrophages recovered from the respiratory epithelial surface before and after reduced GSH (600 mg twice daily for 3 days) aerosol therapy to individuals with IPP. Macrophages were recovered pretherapy and 1 hr after the last doses. Each data point represents the average of two determinations for each individual; a line connects the data points of the same individual.

The pre-therapy levels of total and reduced glutathione in ELF were decreased in IPF compared to normals (total glutathione: IPF 140±13 $\mu$M, normal 270±14 $\mu$M (p=0.002, 11 df); reduced glutathione: IPF 129±13 $\mu$M, normal 245±12 $\mu$M; (p=0.0008, 11 df). In both groups, reduced glutathione was >90% of total ELF glutathione (p=0.9, 11 df). No adverse effects were associated with GSH aerosol administration. Total glutathione in ELF increased 1 hr after the first aerosol (p=0.005; 6 df, FIG. 5). After repeated dosing for 3 days, the average level of total glutathione was higher than the pre-therapy level, but not significantly so (p=0.55). Nonetheless, in all individuals, there was a significant increase in ELF oxidized glutathione compared to baseline (p=0.02, FIG. 6). Plasma glutathione levels in IPF patients were in the normal range (p=0.9) and did not change following aerosolization (p=0.59). In all individuals, there was a decrease in spontaneous $O_2^-$ release by alveolar macrophages (p=0.02) (FIG. 7).

All publications mentioned hereinabove are hereby incorporated in their entirety by reference. Borok et al. (Jul. 27, 1991) Lancet 338:215–216 is also hereby incorporated in its entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for augmenting a decreased level of reduced glutathione in the lungs of a cystic fibrosis patient, comprising administering through inhalation to the lungs of said patient an aerosol of reduced glutathione in a pharmaceutically acceptable carrier in an amount sufficient to effect said augmentation.

2. The method according to claim 1, wherein the aerosol comprises about 10 mg to about 2,500 mg of reduced glutathione.

3. The method according to claim 1, wherein the aerosol comprises about 10 mg to about 25 mg of reduced glutathione per 1 to 5 ml of said pharmaceutically acceptable carrier.

4. The method according to claim 1, wherein the aerosol is produced at about 8 to 12 liters per minute at about 30 to 50 psi of compressed air.

5. The method according to claim 1, wherein the aerosol is produced at about 10 liters per minute at about 40 psi of compressed air.

6. A method for augmenting a decreased level of reduced glutathione in the lungs of a patient seropositive for human immunodeficiency virus, comprising administering through inhalation to the lungs of said patient an aerosol of reduced glutathione in a pharmaceutically acceptable carrier in an amount sufficient to effect said augmentation.

7. The method according to claim 6, wherein the aerosol comprises about 10 mg to about 2,500 mg of reduced glutathione.

8. The method according to claim 6, wherein the aerosol comprises about 10 mg to about 25 mg of reduced glutathione per 1 to 5 ml of said pharmaceutically acceptable carrier.

9. The method according to claim 6, wherein the aerosol is produced at about 8 to 12 liters per minute at about 30 to 50 psi of compressed air.

10. The method according to claim 6, wherein the aerosol is produced at about 10 liters per minute at about 40 psi of compressed air.

11. A method for augmenting a decreased level of reduced glutathione in the lungs of patients with idiopathic pulmonary fibrosis comprising administering through inhalation to the lungs of said patient an aerosol of reduced glutathione in a pharmaceutically acceptable carrier in an amount sufficient to effect said augmentation.

12. The method according to claim 11, wherein the aerosol comprises about 10 mg to about 2,500 mg of reduced glutathione.

13. The method according to claim 11, wherein the aerosol comprises about 10 mg to about 25 mg of reduced glutathione per 1 to 5 ml of said pharmaceutically acceptable carrier.

14. The method according to claim 11, wherein the aerosol is produced at about 8 to 12 liters per minute at about 30 to 50 psi of compressed air.

15. The method according to claim 11, wherein the aerosol is produced at about 10 liters per minute at about 40 psi of compressed air.

* * * * *